United States Patent
Neto

(12) 
(10) Patent No.: US 6,261,323 B1
(45) Date of Patent: Jul. 17, 2001

(54) PROCESS OF COMPOSITION FOR MEDICAL USE

(76) Inventor: Mateus Sommer Neto, Rua Sampaio Viana 299, Rio Comprido-Rio de Janeiro 20261-030 (BR)

(*) Notice: Subject to any disclaimer, the term of this patent is extended or adjusted under 35 U.S.C. 154(b) by 0 days.

(21) Appl. No.: 09/125,483

(22) PCT Filed: Dec. 18, 1997

(86) PCT No.: PCT/BR97/00073

§ 371 Date: Apr. 26, 1999

§ 102(e) Date: Apr. 26, 1999

(87) PCT Pub. No.: WO98/26812

PCT Pub. Date: Jun. 25, 1998

(30) Foreign Application Priority Data

Dec. 19, 1996 (BR) .................................................. 9606075

(51) Int. Cl.⁷ ........................................................ A61F 2/02

(52) U.S. Cl. .................................... 623/23.72; 623/23.73; 623/23.61

(58) Field of Search .............................. 623/23.62, 23.63, 623/23.61, 23.73, 23.75

(56) References Cited

U.S. PATENT DOCUMENTS

| 4,346,099 | * | 8/1982 | Tanouchi | 424/273 |
| 5,344,452 | * | 9/1994 | Lemperle | 623/11 |
| 5,571,182 | | 11/1996 | Ersek et al. | 623/11 |

* cited by examiner

*Primary Examiner*—Michael J. Milano
(74) *Attorney, Agent, or Firm*—Ladas & Parry

(57) ABSTRACT

The present invention uses and implants a composition under the area of the skin where wrinkles occur, said composition being substantially non-absorbable and not subject to rejection or allergic reaction. The composition of the present invention is a colloidal suspension composed of a colloid of carboxygluconate lactic of magnesium and sterile methacrylate microspheres.

4 Claims, No Drawings

PROCESS OF COMPOSITION FOR MEDICAL USE

BACKGROUND OF THE INVENTION

The present application for privilege relates to an original composition process (a chemical formula) of a product for medical use, to mend small hollow parts of the body surface, by means of an injection in the affected tissues, to be used in plastic and esthetic surgery, (especially in creases, wrinkles, lips, nose, hands and other parts), with unique features which are capable of distinguishing it from the state of the art, and having practical and functional benefits, forming a set of conditions which make it deserving the protection saught.

The acrylates were discovered in Germany in 1902 and their medical use in 1935, and for about 12 years they been used in medical repair and esthetics.

The methacrylates are small spheres which need a vehicle to become injectable.

So far, two vehicles have been used for that purpose: 1—Bovine collagen, a long-chain protein, which has a high risk of allergy and can be a virus carrier, as recently accurred with bovine encephalitis. 2—Liquid silicone, which has not yet been approved for general use, as it can cause, siliconomas.

BRIEF SUMMARY OF THE INVENTION

In general, the process which is the object of the present application uses as a vehicle a colloid of an adequate viscosity to the subcutaneous tissues, making possible a practical and safe filling, without the limiting conditions mentioned above.

DETAILED DESCRIPTION OF THE INVENTION

In order to better illustrate this description, reference is made to the composition carboxygluconate lactic of magnesium and methacrylate, which illustrates the process of preparation, so that on a sterile vessel the following substances are placed in adequate proportions to attain the required viscosity: CMC, Ringuer lactate, and EDTA. From time to time the mixture is put into a shaker-mixer and heated to 50° C. for 3 hours, a procedure which must be repeated every 24 hours 4 times. After this period of homogenization, thee methacrylate spheres are added in a sufficient quantity to obtain the desired product. The new mixture is put into a mixer rotating in slow motion for 40 minutes every 12 hours during 3 days. At this stage of the production process calcium gluconate is added. All the contents are subjected to a vacuum and a simultaneous mechanical shaking to eliminate the excess air contained in the Ringuer water. In the final stage, the product is placed in previously sterilized bulbs and again subjected to mechanical shaking for about two hours, after which the bulbs are sealed and subjected to a new sterilization, and finally are cooled to de-condense the humidity on the walls of the bulbs.

What is claimed is:

1. A composition comprising a colloid of carboxygluconate lactic of magnesium and methacrylate.

2. The composition according to claim 1 comprising:
   (a) carboxy methyl cellulose (CMC);
   (b) Ringeur lactate;
   (c) methacrylate;
   (d) ethylenediamine tetracetic acid (EDTA); and
   (e) calcium gluconate.

3. The composition according to claim 1 having a viscosity equivalent to subcutaneous tissue.

4. A process for preparing the composition according to claim 1 comprising the steps of:
   (a) mixing carboxy methyl cellulose (CMC), Ringuer lactate and EDTA to form a mixture;
   (b) agitating the mixture;
   (c) heating the mixture to about 50° C. for about 3 hours;
   (d) repeating as necessary steps (b) and (c);
   (e) adding microspheres of methacrylate;
   (f) adding calcium gluconate; and
   (g) shaking the mixture.

* * * * *